(12) United States Patent
Brown et al.

(10) Patent No.: US 8,329,971 B2
(45) Date of Patent: Dec. 11, 2012

(54) REGENERATION OF CATALYST USED IN PURIFICATION OF AROMATIC STREAMS

(75) Inventors: Stephen H. Brown, Bernardsville, NJ (US); Terry E. Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 289 days.

(21) Appl. No.: 12/758,688

(22) Filed: Apr. 12, 2010

(65) Prior Publication Data

US 2010/0274067 A1 Oct. 28, 2010

Related U.S. Application Data

(60) Provisional application No. 61/171,559, filed on Apr. 22, 2009.

(51) Int. Cl.
*C10G 25/03* (2006.01)

(52) U.S. Cl. ........ 585/276; 585/259; 585/258; 585/273; 585/805

(58) Field of Classification Search ........................ None
See application file for complete search history.

(56) References Cited

U.S. PATENT DOCUMENTS

| | | | |
|---|---|---|---|
| 5,417,844 A | 5/1995 | Boitiaux et al. | |
| 6,368,496 B1 | 4/2002 | Brown et al. | |
| 6,500,996 B1 | 12/2002 | Brown et al. | |
| 6,781,023 B2 | 8/2004 | Brown et al. | |
| 2006/0020154 A1 | 1/2006 | Lo et al. | |
| 2007/0112240 A1* | 5/2007 | Brown et al. | 585/804 |
| 2007/0129235 A1* | 6/2007 | Brown et al. | 502/55 |
| 2008/0249342 A1 | 10/2008 | Iaccino et al. | |
| 2009/0124840 A1 | 5/2009 | Brown et al. | |

FOREIGN PATENT DOCUMENTS

WO 03/059850 7/2003

OTHER PUBLICATIONS

Ivanov et al., "Deactivation by coking and regeneration of zeolite catalysts for benzene-to-phenol oxidation", Applied Catalysts A: General 241 (2003), pp. 113-121.

* cited by examiner

*Primary Examiner* — Tam M Nguyen
(74) *Attorney, Agent, or Firm* — Andrew B. Griffis

(57) ABSTRACT

The invention relates to regeneration of catalysts used in the purification of aromatics streams. It has been surprisingly found that retaining small amount of coke on the catalyst reduces regeneration costs and improves regeneration effectiveness.

10 Claims, No Drawings

REGENERATION OF CATALYST USED IN PURIFICATION OF AROMATIC STREAMS

CROSS REFERENCE TO RELATED APPLICATIONS

This application claims the benefit of Provisional Application No. 61/171,559 filed Apr. 22, 2009, the disclosure of which is incorporated by reference in its entirety.

FIELD OF THE INVENTION

The invention relates to purification of aromatic streams.

BACKGROUND OF THE INVENTION

In petroleum processing, aromatic streams are derived from processes such as naphtha reforming and thermal cracking (pyrolysis). These aromatic streams also contain undesirable hydrocarbon contaminants including mono-olefins, dienes, styrenes and heavy aromatic compounds such as anthracenes.

The aromatic streams are used as feedstocks in various subsequent petrochemical processes. In certain of these processes, such as para-xylene production, e.g., from an aromatic stream containing benzene, toluene and xylene (BTX) or toluene disproportionation, hydrocarbon contaminants cause undesirable side reactions. Therefore the hydrocarbon contaminants must be removed before subsequent processing of the aromatic streams.

Moreover, the shift from high-pressure semiregenerative reformers to low-pressure moving bed reformers results in a substantial increase in contaminants in the reformate derived streams. This in turn results in a greater need for more efficient and less expensive methods for removal of hydrocarbon contaminants from the aromatic streams.

Undesirable hydrocarbon contaminants containing olefinic bonds are quantified by the Bromine Index (BI). Undesirable olefins, including both dienes and mono-olefins, have typically been concurrently removed from aromatic streams such as BTX by contacting the aromatic stream with acid-treated clay. Other materials, e.g., zeolites, have also been used for this purpose. Clay is an amorphous naturally-occurring material, while zeolites used for this purpose generally are synthesized and are therefore more expensive. Both clay and zeolites have very limited lifetimes in aromatics treatment services. The length of service correlates with the level of bromine reactive impurities ("BI-reactive" impurities or contaminants) in the feedstream. BI-reactive contaminants rapidly age both clay and zeolites. Indeed, although clay is the less expensive of the two alternatives, large aromatic plants can spend more than a million dollars a year on clay. Furthermore, since zeolites are considerably more expensive than clay, their use in removing hydrocarbon contaminants can only be justified by dramatically improved stability in aromatics treatment so that their cycle length is practical.

U.S. Pat. Nos. 6,368,496 and 6,781,023 teach bromine reactive hydrocarbon contaminants are removed from aromatic streams by first providing an aromatic feedstream having a negligible diene level. The feedstream is contacted with an acid active zeolite catalyst composition under conditions sufficient to remove mono-olefins. The aromatic stream may be pretreated to remove dienes by contacting the stream with clay, hydrogenation or hydrotreating catalyst under conditions sufficient to substantially remove dienes but not mono-lefins.

U.S. Pat. No. 7,517,824 teach a method of removing hydrocarbon feed residue and regeneration of a catalyst used to reduce BI, but fails to recognize that leaving some coke deposition on the catalyst improves results.

Other relevant references include, U.S. Pat. Nos. 6,500,996; 6,781,023 and U.S. patent application Publications.

Removing trace olefins from the product of refinery naphtha reformers with zeolites is a relatively new commercial process. In the process it is meant to replace, the trace olefins and other contaminants are removed from reformate using acid treated clay. The clay acts as much like a sorbent as like a catalyst. The clay stays on stream for several weeks to many months depending upon the concentration of contaminants. During this time, carbonaceous deposits build up to as much as 40 wt % of the spent "clay" removed from the reactor. The clay and absorbed contaminants are removed from the reactor and sent to landfill. Clay regeneration is not economically practical.

Zeolites used in refining and petrochemical processes are often, but not always, regenerated. Regeneration of zeolites is only practiced if the economics of regeneration are better than the economics of using fresh catalyst. Part of the many considerations include the extent to which burning off the carbon can restore most of the activity. Generally it was heretofore believed that burning off carbon does not restore activity if other contaminants such as metals, steam, or halides have caused irreversible loss of acid sites.

Furthermore, even if the zeolite can be regenerated, it is not obvious that the regeneration can be accomplished at an attractive cost. Regeneration cost is a function of coke on catalyst and regeneration conditions. Spent catalyst with 30 to 40 wt % coke is roughly 5 times more expensive to regenerate than typical spent zeolite catalysts containing closer to 10 wt % coke. Zeolite catalyst used in clay treating deactivates steadily over the course of the cycle as coke deposits on the catalyst and blocks access to the catalytic sites responsible for contaminant removal. The coke on spent MCM-22 catalysts removed from clay treating reactors is typically between 7.5 and 15 wt %. This is surprisingly lower than the 30 to 50 wt % coke typically found on clay removed from aromatics feedstock pretreaters.

There is still a need for an improved method to replace clay treating for the removal of trace olefins from reformate.

The present inventors have surprisingly discovered an improved process of regenerating zeolite catalysts for use in removal of contaminants in an aromatics stream that has the advantages, in embodiments, of the use of milder conditions, while at the same time improving the activity of the regenerated catalyst.

SUMMARY OF THE INVENTION

The invention is directed to processes for removing trace olefins from aromatic feeds and more particularly for regenerating zeolite catalyst to be used in said processes. It has been surprisingly found that retaining small amount of coke on the catalyst reduces regeneration costs and improves regeneration effectiveness.

It is an object of the invention to decrease the cost of regeneration of zeolite catalysts for use in removing BI-reactive contaminants from an aromatic feedstream, while at the same time improving the activity of the regenerated catalyst.

These and other objects, features, and advantages will become apparent as reference is made to the following detailed description, preferred embodiments, examples, and appended claims.

DETAILED DESCRIPTION

According to the invention, a process for the purification of aromatic streams is provided that includes regeneration of the catalysts used in the purification of said aromatics streams, more particularly wherein said purification is for the purpose of removing BI-reactive contaminants and/or contaminants that are to be avoided in downstream processing of BTX streams.

It has been surprisingly found that retaining small amount of coke on the catalyst reduces regeneration costs and improves regeneration effectiveness.

The process will be described with particular emphasis on feeds, pretreatment, catalysts, process conditions, and regeneration. One of ordinary skill in the art will recognize that there are numerous variations possible within the scope of the appended claims.

Feeds

Aromatic streams can be obtained from reforming and cracking processes. In embodiments, the streams include, e.g., mononuclear aromatic hydrocarbons and undesirable olefins including styrenes, and the streams have an initial Bromine Index (BI) from about 100 to about 3000. The Bromine Index is an indicator of the presence of olefinic bonds. Bromine Index is determined according to ASTM D 2710-92 and is a measure of milligrams of bromine consumed by 100 grams of sample under given conditions.

The aromatics include, for example, benzene, toluene, xylene, ethyl benzene, cumene and other aromatics derived, e.g., from reformate. Reformate is separated by distillation into light reformate which is mostly benzene and toluene, and heavy reformate which includes toluene, ortho-, meta- and para-xylenes and other heavier aromatics including C9+. Some aromatic streams such as heavy reformate derived from semi-regen processes contain negligible levels of dienes as they emerge from the processing. By negligible is meant that the level is below 50 ppm, essentially diene-free or too low to be quantified. Other aromatic streams such as light reformate derived from semi-regen reformers and light and heavy reformate from CCR's (continuous catalyst regeneration) processes include detectable levels of dienes, e.g., over 50 ppm, as they emerge from the processes.

The aromatic streams to be treated according to the invention contain bromine-reactive hydrocarbon compounds in levels which interfere in subsequent aromatics processing. An objectionable level of olefinic contaminants is from about 0.05 to about 1.5 weight percent or a BI from about 100 to about 3000.

According to embodiments of the invention, use of a regenerated catalyst improves the removal of olefinic contaminants in the aromatic streams so that said contaminants do not interfere in subsequent aromatics processing.

PRE-TREATMENT: an aromatic hydrocarbon stream to be treated to remove mono-olefins according to the invention is essentially diene-free, i.e., has a negligible level of dienes. If the aromatic stream contains dienes above these levels, the stream can be pretreated according to the invention to remove the dienes. Dienes are more selective for catalyst deactivating coke formation than mono-olefins. Therefore, these highly reactive diene species are substantially removed over a first catalyst. One of ordinary skill in the art in possession of the present disclosure can determine the appropriate level of dienes present without more than routine experimentation. In embodiments, the amount of dienes will be less than 1000 ppm and a feed such as reformate having less than 1000 ppm dienes is preferred. Another preferred feed is one having 10,000 ppm total olefins, including styrenes and dienes, wherein the dienes are present in the amount of no more than 10 wt % of the total BI. Feeds having less than 1000 ppm or less than 500 ppm or less than 300 ppm or less than 100 ppm dienes are also preferred. There is no particular minimum amount of dienes that needs to be specified, however in embodiments it will be specified that dienes are present, or that dienes are present in the amount of at least 1 ppm, or 10 ppm, or 100 ppm. In a process according to the invention, the catalyst has excellent stability even for commercial feeds having the highest diene levels to be expected.

The conditions can be determined by one of skill in the art in possession of the present disclosure without more than routine experimentation, however conditions for the pre-treating step are conducted at temperatures preferably of about 50 or 100° F. (10 or 38° C.) to about 500° F. (260° C.), more preferably about 150° F. (66° C.) to about 450° F. (232° C.). A weight hourly space velocity (WHSV) is preferably from about 0.1 to about 10 and the pressure is preferably about 50 psig to about 500 psig. The pre-treating is advantageously carried out in the absence of added hydrogen. Preferred catalysts for the pretreatment step include acid treated clay such as bentonite or traditional base metal-containing hydrogenation or hydrotreating catalysts such as NiMo/$Al_2O_3$, CoMo/$Al_2O_3$, Ni/$Al_2O_3$ and Ni/$SiO_2$.

The pre-treated aromatic feed is then treated over a second catalyst to substantially remove the mono-olefins.

The catalyst for selectively removing mono-olefin compounds are those per se known in the art and include, e.g., large pore zeolites, particularly preferred, for purposes of the present invention, MCM-22 type materials, mesoporous materials including those termed M41 S, SAPO's, pillared and/or layered materials.

Zeolites are divided into three major groups according to their pore/channel systems. These systems include 8-membered oxygen ring systems, 10-membered oxygen ring systems, 12-membered oxygen ring systems, and the dual pore systems including 10 and 12-membered oxygen ring openings. In general, they are referred to as small, medium or large pore size zeolites proceeding from 8 to 12 membered systems. These systems are more completely described in Atlas of Zeolite Structure Types, International Zeolite Assoc., Polycrystal Book Service, Plattsburg, 1978.

The chemical composition of zeolites can vary widely and they typically consist of $SiO_2$ in which some of the silicon atoms may be replaced by tetravalent ions such as Ti or Ge, or by trivalent ions such as Al, B, Ga, Fe, or by bivalent ions such as Be, or by other members of Group III of the Periodic table of the Elements or by a combination of the aforementioned ions. When there is substitution by bivalent or trivalent ions, cations such as Na+, $Ca^{++}$, $NH_4^+$ or H+ are present in the as-synthesized zeolite, also organic ions such as tetramethylamine ($TMA^+$), tetraethylamine ($TEA^+$) and others. The organics are typically removed by calcination prior to use of the zeolite. Ion exchange of residual cations with, for example, $NH_4^+$, is generally followed by calcination to produce the acidic zeolite.

Preferred catalysts include natural or synthetic crystalline molecular sieves, with ring structures of ten to twelve members or greater. Crystalline molecular sieves useful as catalysts include as non-limiting examples, large pore zeolites ZSM-4 (omega) (U.S. Pat. No. 3,923,639), mordenite, ZSM-18 (U.S. Pat. No. 3,950,496), ZSM-20 (U.S. Pat. No. 3,972,983), zeolite Beta (U.S. Pat. Nos. 3,308,069 and Re 28,341), Faujasite X (U.S. Pat. No. 2,882,244), Faujasite Y (U.S. Pat. No. 3,130,007), USY (U.S. Pat. Nos. 3,293,192 and 3,449,070), REY and other 15 forms of X and Y, MCM-22 (U.S. Pat. No. 4,954,325), MCM-36 (U.S. Pat. No. 5,229,341), MCM- 49 (U.S. Pat. No. 5,236,575), MCM-56 (U.S. Pat. No. 5,362, 697) and mesoporous materials such as M41S (U.S. Pat. No. 5,102,643) and MCM-41 (U.S. Pat. No. 5,098,684). More preferred molecular sieves include 12 membered oxygen-ring structures ZSM-12, mordenite, Zeolite Beta, USY, and the mixed 10-12 membered oxygen ring structures from the MCM-22 family, layered materials and mesoporous materials. Most preferred are the MCM-22 family of molecular sieves. This family, i.e., MCM-22 type materials, includes, e.g., MCM-22, MCM-36, MCM-49 and MCM-56. The MCM-22 type materials may be considered to contain a similar common layered structure unit. The structure unit is described, e.g., in U.S. Pat. Nos. 5,371,310, 5,453,554, 5,493, 065 and 5,557,024.

One measure of acid activity may be termed the Alpha Value. The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.16 sect$^{-1}$). The alpha test is described in U.S. Pat. No. 3,354,078, in the Journal of Catalysis, Vol. 4, p. 527 (1965); Vol. 6, p. 278, and Vol. 61, p. 395 (1980), each incorporated by reference as to that description. The experimental conditions of the test used herein include a constant temperature of 538° C. and a variable flow rate as described in the Journal of Catalysis, Vol. 61, p. 395 (1980). In embodiment, the catalysts have an alpha value from about 100 to about 1000.

The crystalline molecular sieve may be used in bound form, i.e., composited with a matrix material, including synthetic and naturally occurring substances, e.g., clay, silica, alumina, zirconia, titania, silica-alumina and other metal oxides. Naturally-occurring clays include those of the montmorillonite and kaolin families. The matrix itself may possess catalytic properties, often of an acid nature. Other porous matrix materials include silica-magnesia, silica-zirconia, silica-thoria, silica-beryllia, silica-titania, as well as ternary compositions such as silica-alumina-thoria, silica-alumina-zirconia, silica-alumina-magnesia, and silica-alumina-zirconia. A mixture of these components can also be used. The relative proportions of crystalline molecular sieve material and matrix may vary widely from 1 to 90 weight percent, usually about 20 to about 80 weight percent. The catalyst can also be used in the absence of matrix or binder, i.e., in unbound form. The catalyst can be used in forms per se known, preferably in the form of an extrudate, lobed form (e.g. trilobe), spheres, spray-dried microspheres, or powder.

In general, the method for the removal of mono-olefins is carried out under conditions including a moderately elevated temperature, preferably ranging from about 200 or 250° F. (93 or 121° C.) to about 500° F. (260° C.) more preferably from about 250° F. (121° C.) to about 450° F. (232° C.); a space velocity preferably ranging from about 0.1 WHSV to about 100 WHSV, more preferably from about 1 WHSV to about 30 WHSV; and a pressure ranging from about 50 psig to about 1000 psig, more preferably about 100 psig to about 500 psig.

The following experiments are meant to be exemplary of the present invention and should not be taken to be limiting thereof.

Spent MCM-22 zeolite catalyst from a commercial xylenes treater was analyzed before regeneration. The amount of coke deposited can be determined by method per se known in the art. In the present case the amount of coke both before and after regeneration was determined by use of the LECO CR-412 Carbon Analyzer, Model #602-100. In all cases described herein the amount of carbon is described relative to the amount of zeolite, as the clay is discarded and not treated as described herein. One of ordinary skill in the art in possession of the present disclosure would recognize, therefore, that the specific ratio of zeolite to clay is not significant as regards the regeneration experiments, but would apply to any ratio of zeolite to clay. The samples contained 10-15 wt % carbon, 2000-5000 ppm chlorides, and 1000-5000 ppm iron. The carbon on the catalyst is within normal range and lower than expected based on experience with clay. The discovery of significant quantities of chloride and iron caused concern, as both elements are known to be able to cause irreversible catalyst deactivation. Chloride was a major concern because it is a known contaminant in reformate feedstocks. From this analysis it was not obvious that regeneration according to the present invention would be successful.

Example 1

A commercial unit was loaded with 55 vol % MCM-22 catalyst and 45 vol % clay. The feedstock was produced by distilling the liquid product obtained from a refinery CCR to obtain a C8+ heavy reformate. The feedstock had a BI ranging from 750 to 1500 and contained <10 ppm benzene, <5000 ppm toluene, and >50 wt % C8 aromatics. The feedstock was processed over the catalyst system at 1.2 LHSV, 200 psig, and 185 to 205° C. The catalyst operated for 18 months before it lost sufficient activity to maintain the target reduction of contaminants.

Example 2

The spent MCM-22 zeolite catalyst from Example 1 was regenerated at 540° C., 20 psia, and 4 psia steam. The low carbon on catalyst and severe conditions resulted in a rapid regeneration. Careful control of the conditions, within the skill of the ordinary artisan in possession of the present disclosure without more than routine experimentation, resulted in a regenerated catalyst that remained dark gray to black and still contained 0.5 to 1.0 wt % carbon. Surprisingly, retaining 0.5 to 1.0 wt % coke both reduces regeneration cost and improves regeneration effectiveness. Samples of the regenerated catalyst were analyzed and proven to have near equal activity to the fresh catalyst placed in the same commercial xylenes treater, as discussed below.

Example 3

All the regenerated catalyst from Example 2 was reloaded into the same xylenes treater along with make-up MCM-22 catalyst and fresh clay catalyst. The ratio of MCM-22 catalyst to clay was 55 vol % to 45 vol %, the same as in example 1. The only significant difference between example 1 and example three was the use of regenerated catalyst. A second cycle was completed. The second cycle was also 18 months. Thus the regeneration was considered to be successful. Note that the second cycle was approximately four times longer than even the most successful example in U.S. Pat. No. 7,517, 824.

Before this experiment was carried out, it was impossible to know whether catalysts for reducing the BI content of aromatics feedstocks could be successfully regenerated multiple times in the simple manner set forth herein. This was especially true for heavy reformate feedstocks used to produce xylenes in aromatics plants. Heavy reformate feedstocks are known to contain chlorides which are believed to irreversibly deactivate catalysts. Since zeolite catalyst is more expensive than clay, in order to be more economically attractive, the zeolite catalyst should be able to be regenerated and reused for multiple cycles.

Additional experiments were carried out to illustrate the general applicability of the present invention.

Three samples (A, B, and C) of spent MCM-22 zeolite catalyst from a commercial benzene extract treater have been regenerated at 540° C., 20 psia (total pressure), and 4 psia steam. Steam partial pressure is controlled by drying the air feedstock by chilling it to condense contained moisture. Unit pressure control is used to maintain a steady airflow through the unit. Flowing air too fast can cause coke to burn too fast which can create hot spots. Use of multiple thermocouples along the length of the regeneration vessel allows continuous monitoring of catalyst temperatures. By adjusting air flow and using inert quench gas if necessary, hotspots are avoided. One of ordinary skill in the art in possession of the present disclosure can make the appropriate adjustments to achieve the advantages of the present invention without more than routine experimentation. Regenerated catalyst was produced that remained dark gray to black and still contained 0.5 to 3.0 wt % carbon, and in embodiments 0.5 to 1.0 wt % carbon. Surprisingly, retaining 0.5 to 3.0 wt % coke both reduces regeneration cost and improves regeneration effectiveness.

Performance is monitored by tracking run length and the amount of olefins removed (based on BI). The results are provided in Table 1. Second cycle performance for catalysts A and B resulted in longer run lengths but lower values of olefins removed. The state of the catalyst was assessed using a model feedstock for clay treating consisting of benzene and propylene. A standard weight of catalyst, benzene, and propylene were loaded into an autoclave. The autoclave is sampled with time in order to assess propylene disappearance vs. time. The data is plotted to determine the activity of the catalyst for alkylation of benzene with propylene. After one regeneration the catalysts showed between 81 and 93% of fresh catalyst activity. Catalyst batch A has been regenerated a second time and tested again using the benzene/propylene feedstock. The twice regenerated material has 71% of fresh activity. Like Examples 1-3 set forth above, the most important result is that the data shows that the catalyst is not irreversibly deactivated by the reaction conditions but can still produce commercially acceptable results. The extracted benzene feed does not deposit contaminants on the catalyst that irreversibly damage the catalyst during the reaction or during the regeneration. The data also shows that regeneration at relatively severe conditions is not causing irreversible deactivation. Finally, the data shows that catalyst performance in olefin removal service is as good or better than expected based on model compound activity testing.

The results of the activity tests are shown in Table 1, below.

As shown above, three batches of catalyst, A, B, and C, have been tracked in a single unit that removes bromine reactive contaminants from an aromatics feedstock produced in a benzene extraction unit. Catalysts A and B were used in two aromatics removal cycles and regenerated twice. Performance for aromatics feed pretreatment is measured in cycle length in days. The second cycles were longer than the first cycles for all three batches. Since cycle lengths depend upon feedstock BI content as well as the condition of the catalyst, it is not surprising to see large variability in days on line. A second measure of regeneration success is the activity of the catalyst at standard conditions. The activity of the fresh catalyst is compared with the activity of regenerated catalyst. Generally, catalyst activity declines with the number of regenerations. Catalyst A has been regenerated twice. After one regeneration the catalyst had 93% of fresh activity and after two regenerations had 71% of fresh activity. Catalyst cycle length is typically less dependent upon regeneration than fresh catalyst activity. Test also showed that in each case the catalyst can be regenerated at least 10 times and still remain useful for aromatics feed BI reduction to meet commercially acceptable targets. Surprisingly, nothing in the benzene extract feedstock that deposits on the catalyst with time on stream irreversibly deactivates the catalyst either during the run itself or during regeneration.

The invention has been described above with reference to numerous embodiments and specific examples. Many variations will suggest themselves to those skilled in this art in light of the above detailed description. All such variations are within the full intended scope of the appended claims. Nevertheless, preferred embodiments include the following: in a method of regenerating a zeolite catalyst used to purify aromatic feeds, the improvement comprising treating said zeolite catalyst under conditions sufficient so that said catalyst retains 0.5 to 3.0 wt % carbon, preferably 0.5 to 1.0 wt % carbon, which may be further limited by preferred treatment conditions including the following: temperatures of 400° C. to 600° C., pressures of 10 psia to 30 psia (total pressure), and in the presence of steam, and/or wherein said zeolite catalyst comprises a catalyst from the MCM-22 family of molecular sieves. Another particularly preferred embodiment is a method for removing bromine-reactive contaminants from an aromatic hydrocarbon feedstream which comprises: (a) providing an aromatic hydrocarbon feedstream containing bromine-reactive contaminants; (b) contacting the feedstream with an acid active catalyst composition under conditions sufficient to only partially remove bromine-reactive contaminants to provide both a treated aromatic hydrocarbon feedstream and a used acid active catalyst composition having carbon deposits thereon; and (c) removing said used acid active catalyst composition and regenerating by treating said used catalyst under conditions sufficient to partially remove said carbon deposits and provide a regenerated catalyst char-

TABLE 1

| Extract Treater Cycle | Catalyst in Service | Catalyst Batch | Fresh Catalyst Make-up (%) | Normalized Activity as Loaded* (%) | Run Length (days) | Normalized Activity after Regeneration (%) |
| --- | --- | --- | --- | --- | --- | --- |
| 1 | Fresh | A | — | 100 | 98 | 93 |
| 2 | Fresh | B | — | 100 | 119 | 86 |
| 3 | Fresh | C | — | 100 | 183 | 81 |
| 4 | Regen | 100% A | 0 | 93 | 150 | 71 |
| 5 | Regen | 87% B | 13 | 88 | 349 | NA |
| 6 | Regen | 92% C | 8 | 83 | in service | NA |

*100% activity assumed.

acterized by the presence of 0.5 to 3.0 wt % carbon, preferably 0.5 to 1.0 wt % carbon, particularly wherein said method further comprises contacting said regenerated catalyst with an aromatic hydrocarbon feedstream, whereby bromine-reactive contaminants are removed from said feedstream. Anyone of these embodiments may be limited by one or more of the following most preferred conditions for regeneration: a temperature of from 400 to 600° C., a pressure of from 10 to 50 psia (or 15 to 30 psia, or 10 to 30 psia, or 15 to 50 psia, total pressure), air flow at the rate of from 0.1 to 10 WHSV, and in more preferred embodiments having an oxygen content of 1 to 20 wt % and/or the limitation that the catalyst be at least one from the MCM-22 family of molecular sieves. One of skill in the art, having the present invention before them, can determine any additional requirements for the above-specified requirements without undue experimentation. Also preferred is a method comprising: (a) providing an aromatic hydrocarbon feedstream containing bromine-reactive contaminants (particularly a feedstream having a BI of 600 or greater, such as 600-1000 or 750 to 1500, and preferably one also characterized as containing <10 ppm benzene, <5000 ppm toluene, and >50 wt % C8 aromatics); (b) contacting said feedstream with a catalyst composition comprising at least one zeolite under conditions sufficient to at least partially remove bromine-reactive contaminants from said feedstock, so as to provide a treated aromatic hydrocarbon feedstream having a BI at or below a preselected value (such as 50 or 100), and a catalyst composition having carbon deposits on said zeolite as a result of said contacting, wherein said carbon deposits are in the amount of greater than 3.0 wt %, based on the weight of said zeolite; and then (c) treating said zeolite under conditions sufficient to only partially remove said carbon deposits, said conditions including flowing heated air comprising molecular oxygen over said zeolite at a WHSV sufficient so as to provide a regenerated zeolite characterized by the presence of 0.5 to 3.0 wt % carbon, based on the weight of said zeolite; and also even more preferred embodiments selected from one or more of the following: (1) wherein said conditions including a temperature of from 400 to 600° C., a pressure of from 10 to 50 psia (total pressure), and a WHSV of from 0.1 to 10; (2) wherein said regenerated catalyst is characterized by the presence of 0.5 to 1.0 wt % carbon; (3) said method further comprising repeating steps (a) through (c) a plurality of times (such as wherein step (b) achieves the preselected BI value for at least one year for a plurality of times); (4) wherein said air is characterized by a molecular oxygen content of 1 to 20 wt %; (5) wherein said zeolite is at least one selected from the MCM-22 family of molecular sieves; (6) wherein said zeolite is selected from the MCM-22 family of zeolites, and wherein, in addition to said greater than 3 wt % carbon deposited thereon, 2000-5000 ppm chloride and 1000-5000 ppm iron are also present on said zeolite as a result of removal of bromine-reactive contaminants from said aromatic hydrocarbon feedstream in step (b); (7) wherein greater than 5 wt % to 20 wt % carbon is present on said zeolite as a result of removal of bromine-reactive contaminants from said aromatic feedstream in step (b), wherein the BI of said aromatic hydrocarbon feedstream in step (a) is at least 600 and said preselected BI in step (b) is no greater than 50 (or in embodiments, 100), and then after step (c), repeating steps (a) through (c) a plurality of times (particularly wherein the preselected value (such as 50 or 100) is achieved a plurality of times for at least a year); (8) including a step of measuring the amount of carbon (and/or chloride and/or iron) deposited on said zeolite after step (c) and/or measuring the amount of carbon (and/or chloride and/or iron) deposited on said zeolite before said contacting in step (b); and finally (9) including a separate step, between steps (b) and (c), of steam stripping hydrocarbon from said zeolite.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A method comprising:
   (a) providing an aromatic hydrocarbon feedstream containing bromine-reactive contaminants;
   (b) contacting said feedstream with a catalyst composition comprising at least one zeolite under conditions sufficient to at least partially removed bromine-reactive contaminants from said feedstock, so as to provide a treated aromatic hydrocarbon feedstream having a BI at or below a preselected value, and a catalyst composition having carbon deposits on said zeolite as a result of said contacting, wherein said carbon deposits are in the amount of greater than 3.0 wt %, based on the weight of said zeolite; and then
   (c) treating said zeolite under conditions sufficient to only partially remove said carbon deposits, said conditions including flowing heated air comprising molecular oxygen and steam over said zeolite at a WHSV sufficient so as to provide a regenerated zeolite characterized by the presence of 0.5 to 3.0 wt % carbon, based on the weight of said zeolite, said conditions in (c) further including a temperature of from 400 to 600° C.

2. The process of claim 1, wherein said conditions including a pressure of from 10 to 50 psia (total pressure), and a WHSV of from 0.1 to 10.

3. The method of claim 1, wherein said regenerated catalyst characterized by the presence of 0.5 to 1.0 wt % carbon.

4. The method of claim 1, further comprising repeating steps (a) through (c) a plurality of times.

5. The method of claim 1, wherein said air is characterized by a molecular oxygen content of 1 to 20 wt %.

6. The method according to claim 1, wherein said catalyst is at least one selected from the MCM-22 family of molecular sieves.

7. The method of claim 1, wherein said zeolite is selected from the MCM-22 family of zeolites, and wherein, in addition to said greater than 3 wt % carbon deposited thereon, 2000-5000 ppm chloride and 1000-5000 ppm iron are also present on said zeolite as a result of removal of bromine-reactive contaminants from said aromatic hydrocarbon feedstream in step (b).

8. The method of claim 1, wherein greater than 5 wt % to 20 wt % carbon is present on said zeolite as a result of removal of bromine-reactive contaminants from said aromatic feedstream in step (b), wherein the BI of said aromatic hydrocarbon feedstream in step (a) is at least 600 and said preselected BI in step (b) is no greater than 50, and then after step (c), repeating steps (a) through (c) a plurality of times.

9. The method of claim 1, including a step of measuring the amount of carbon deposited on said zeolite after step (c).

10. The method of claim 1, wherein said carbon deposits in step (b) are in the amount of from 10 to 15 wt %, based on the weight of said zeolite.

* * * * *